US007130534B1

(12) United States Patent
Miller, II

(10) Patent No.: US 7,130,534 B1
(45) Date of Patent: Oct. 31, 2006

(54) GAS CHROMATOGRAPH HAVING A RADIANT OVEN FOR ANALYTICAL DEVICES

(75) Inventor: Sammye E. Miller, II, New Castle, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/111,111

(22) Filed: Apr. 21, 2005

(51) Int. Cl.
*H05B 3/00* (2006.01)
*G01N 30/60* (2006.01)

(52) U.S. Cl. ............... 392/416; 392/435; 219/759; 219/762; 73/23.35

(58) Field of Classification Search ........ 219/678–679, 219/759, 730, 710–712, 762; 73/23.35–23.4; 422/21, 89; 392/416, 435
See application file for complete search history.

(56) References Cited

U.S. PATENT DOCUMENTS 5,808,178 A * 9/1998 Rounbehler et al. ........ 73/23.39
5,939,614 A * 8/1999 Walters et al. ............. 73/23.39

FOREIGN PATENT DOCUMENTS

| GB | 908793 | * | 10/1962 |
| JP | 60-211947 | * | 10/1985 |
| SU | 1654798 | * | 6/1991 |

* cited by examiner

*Primary Examiner*—Philip H. Leung

(57) ABSTRACT

A radiant oven comprises a radiant energy source configured to provide radiant electromagnetic energy, an insert configured to receive the radiant electromagnetic energy and convert the radiant electromagnetic energy into heat, and an additional element configured to receive the heat.

9 Claims, 6 Drawing Sheets

GAS CHROMATOGRAPH HAVING A RADIANT OVEN FOR ANALYTICAL DEVICES

BACKGROUND

Many chemical separation analyses, such as gas and liquid chromatography, require the chemical sample to be temperature-controlled throughout the analysis.

A chromatograph comprises an inlet where the sample is introduced, an oven containing an analytical column where the separation takes place, and a detector where the constituents of the sample are detected and recorded. Each of these parts of the instrument is temperature-controlled to ensure the integrity and repeatability of the analysis. An analysis performed at a constant controlled temperature is referred to as isothermal. To perform an isothermal analysis, the analytical column is typically placed in a temperature-controlled chamber, often referred to as an oven that is preheated to the desired temperature. A non-isothermal analysis, where the column temperature is gradually raised over time, is also common, especially for samples with relatively massive components that would otherwise take a long time to elute from the column.

Conventional chromatographic ovens typically use convection technology to heat and maintain the interior of the chamber, and hence the column, at the desired temperature. However, conventional ovens are relatively large in comparison to an analytical column which they are intended to heat and, as a result, are very power inefficient. In addition to cost, a side effect of power inefficiency is that the oven is slow to heat and cool, resulting in reduced sample throughput and productivity.

One prior solution to reduce power consumption when heating an analytical column is to use a resistively heated analytical column. Unfortunately, this technology requires a specially fabricated column that may be incompatible with existing chromatography systems. In addition, an analytical column is susceptible to contamination at its input usually due to sample build-up over time. The contaminated portion of the analytical column is typically removed so the column can be reused. This is difficult or impossible to do when using a resistively heated column since the column and heating element are bundled together. Further, it is difficult to precisely determine the temperature of a resistively heated analytical column because it is difficult to place a temperature probe so that its temperature tracks the temperature of the resistively heated column precisely.

Another prior solution to reduce power consumption when heating an analytical column is to use an electromagnetic (EM) radiant source, such as a microwave or infrared source. Unfortunately, capillary columns, which represent the overwhelming majority of analytical columns used in gas chromatographic analyses today, are typically fabricated from fused silica glass, which is transparent to radiant energy. To take advantage of being heated by radiant energy the analytical column must be coated, or otherwise treated, with a material or substance that can absorb the radiation emitted from the radiant source and convert the radiant energy to heat. Also, as with the resistively heated analytical column, determining the precise temperature of an analytical column heated by a radiant source is difficult because it is difficult to ensure that a temperature probe absorbs and converts the radiant energy to heat in the same way as the column to provide an accurate measure of the column temperature. Finally, the directional or "line-of-sight" nature of an EM radiant source adds a potential source of temperature gradients across the column that would not be present in a conventional convection oven.

Therefore, it would be desirable to efficiently heat a conventional analytical column and accurately determine its temperature.

SUMMARY OF INVENTION

According to one embodiment, a radiant oven comprises a radiant energy source configured to provide radiant electromagnetic energy, an insert configured to receive the radiant electromagnetic energy and convert the radiant electromagnetic energy into heat, and an additional element configured to receive the heat.

Other embodiments and methods of the invention will be discussed with reference to the figures and to the detailed description of the preferred embodiments.

Brief Description of the Figures

The invention will be described by way of example, in the description of exemplary embodiments, with particular reference to the accompanying figures.

DETAILED DESCRIPTION

While described below for use in a gas chromatograph, the radiant oven to be described below can be used in any analysis application where it is desirable to quickly and efficiently heat and cool an analytical column or other device.

Figure 1:
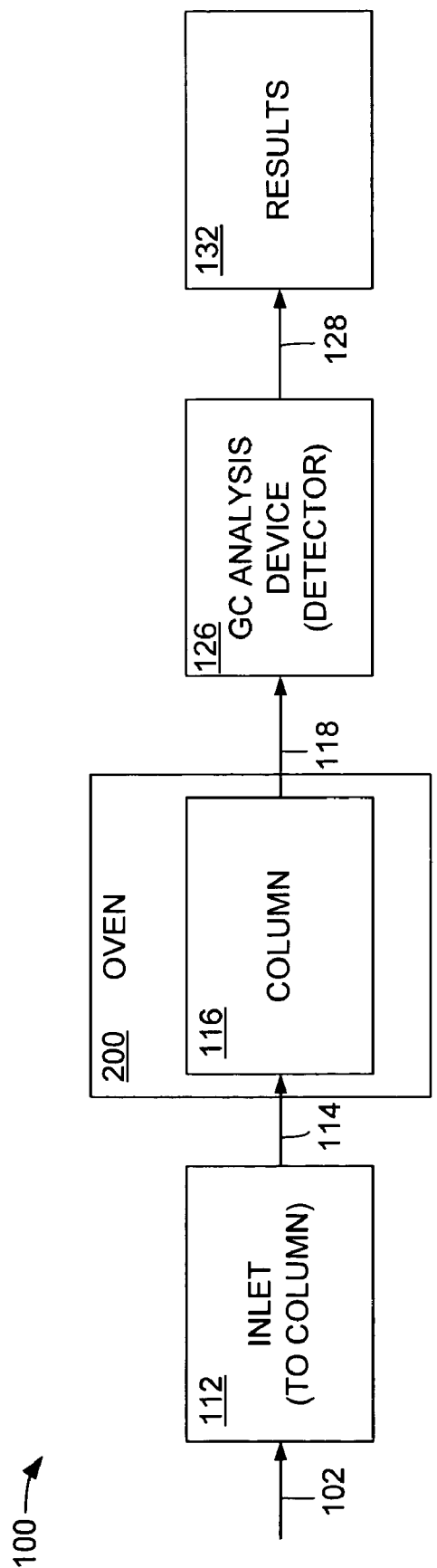
FIG. 1 is a schematic diagram illustrating a simplified chromatograph in which a radiant oven constructed in accordance with an embodiment of the invention may reside.

FIG. 1 is a block diagram illustrating a simplified gas chromatograph 100, which is one possible device in which the radiant oven of the invention may be implemented. The radiant oven of the invention may also be used in any gas phase sampling device or in any analytical device, and may also be useful for liquid chromatography applications. In addition, the radiant oven can be used in a stand-alone application. The radiant oven can be used to quickly and efficiently heat a capillary column, a packed column, or other analytical apparatus.

The gas chromatograph 100 includes an inlet 112, which receives a sample of material to be analyzed via connection 102 and provides the sample via connection 114 to, for example, a chromatographic column 116, also referred to as a capillary column, an analytical column, or just a column. To effectively separate compounds of interest during chromatography, the analytical column 116 may be heated to temperatures well above ambient temperature. The temperature to which the analytical column 116 is heated is dependent on the type of sample being analyzed and may vary during a sample run to analyze multiple compounds and elements from a single sample. Accordingly, the analytical column 116 is located in a temperature chamber, also referred to as an oven. In this example, the oven is a radiant oven 200 constructed in accordance with embodiments of the invention.

The output of the column 116 is connected via connection 118 to a detector 126 in the gas chromatograph 100. The output of the detector 126, via connection 128 is a signal representing the result 132 of the analysis.

Figure 2:
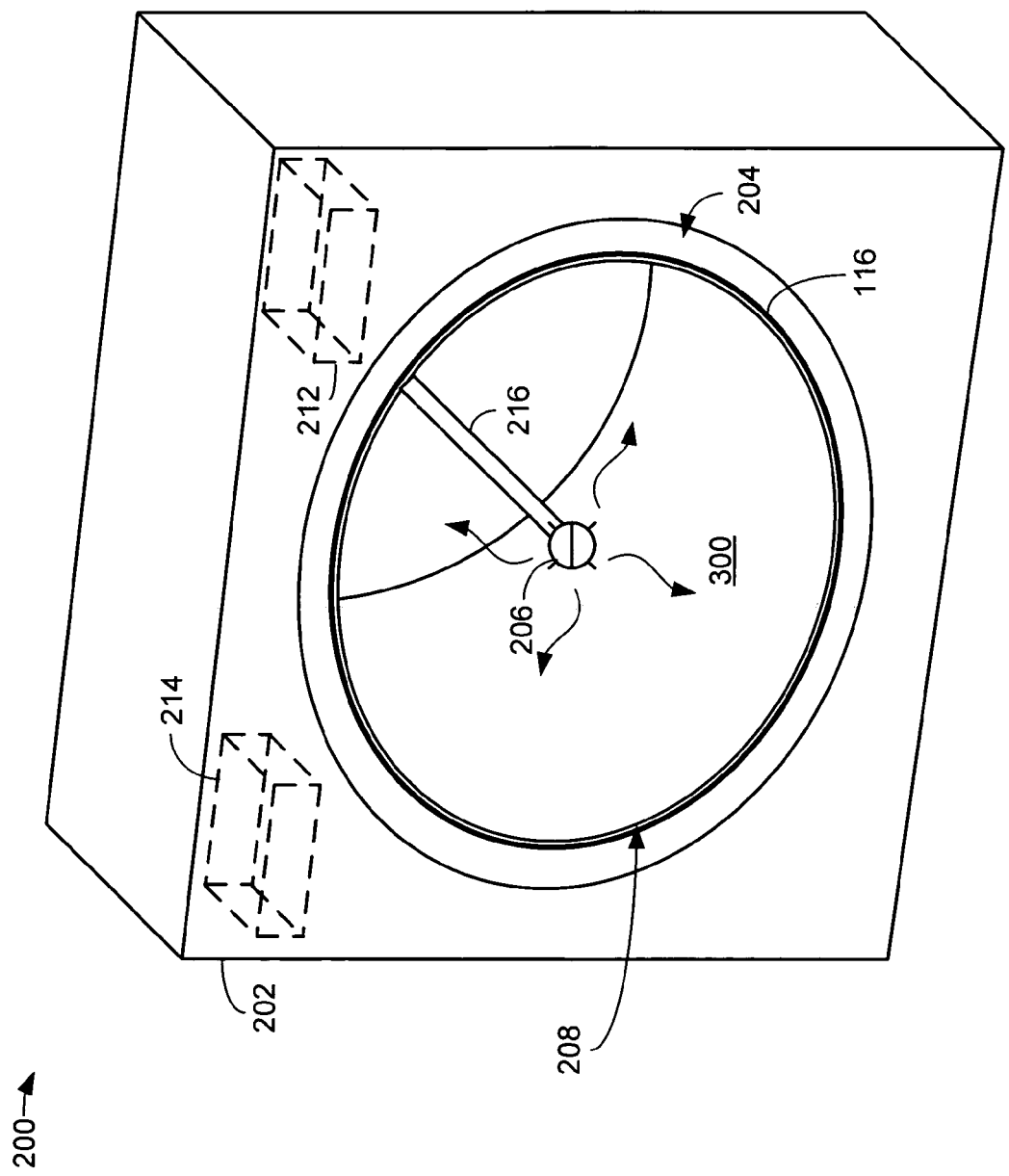
FIG. 2 is a schematic diagram illustrating a perspective view of an embodiment of the radiant oven of FIG. 1.

FIG. 2 is a schematic diagram illustrating a perspective view of an embodiment of the radiant oven 200 of FIG. 1. The radiant oven 200 includes a housing 202 having a recess 204. The recess 204 is configured to releasably receive an insert 300. The insert 300 is also sometimes referred to as a basket. An analytical column 116, which in this example is a chromatographic column, is wrapped around the insert 300 so that the analytical column 116 can be efficiently and uniformly heated and cooled in the oven 200. The analytical column 116 can be either tightly or loosely wrapped around the outer surface of the insert 300, depending on application. In one embodiment, the analytical column 116 is tightly wrapped around the insert 300 to minimize the amount of exposed column surface area so that heat absorption is maximized. The input and output of the analytical column 116 is omitted for drawing clarity. A temperature sensor 208 can be secured to the outer surface of the insert 300 to precisely determine the temperature of the insert 300 and the analytical column 116.

The oven 200 also includes a radiant source 206 and control circuitry 212 configured to control the duty cycle of the power supplied to the radiant source. The control circuitry 212 uses information fed back from the temperature sensor 208 to determine the power required to achieve and maintain the temperature in the radiant oven 200 at a set point prescribed by the analysis. The duty cycle is the fraction of ON time of the radiant source relative to the total cycle (ON+OFF) time. In addition to controlling the duty cycle of the radiant source 206 it is often important to control the total cycle time as well. For example, a duty cycle of 20% can be achieved with an ON time of 2 minutes vs. a total time of 10 minutes or an ON time of 2 seconds vs. a total time of 10 seconds, etc. Although the duty cycle is the same, the total cycle times are quite different. The total cycle time (10 minutes, 10 seconds, 10 milliseconds, etc.) plays an important role for radiant sources having fast reaction times such as a quartz halogen infrared (IR) radiant source. When the total cycle time is too long for a quartz halogen IR radiant source, the filament can cool significantly between cycles. Repeated heating and cooling of the filament in a quartz halogen IR radiant source causes fatigue and shortens the life of the filament. Many quartz halogen radiant source manufacturers suggest using "phase-angle fired" control where the total cycle time can be as small as a fraction of one cycle of the AC input power.

The radiant oven 200 optionally includes a fan 214, or other means for quickly cooling the oven 200. The radiant source 206 can be mounted on a pedestal 216. In one embodiment, the radiant source 206 is a quartz halogen IR bulb having a cylindrical profile. However, the shape of the radiant source 206 may differ. The radiant source can be an infrared (IR) source as mentioned above, a microwave source, an ultraviolet (UV) source, a visible (VIS) source, an X-ray source, or any other electromagnetic (EM) radiant source. In addition, the radiant source 206 may be one that emits radiant EM energy at multiple wavelengths, one that emits radiant EM energy at a single wavelength, such as a laser, and one that emits both visible and invisible IR, UV, or any combination thereof. A cover is omitted from the radiant oven 200 for clarity.

Because the analytical column 116 is typically fabricated from fused silica, which is transparent to EM radiant energy, the radiant EM energy output of the radiant source 206 must be converted to heat to be transferred to the analytical column 116. In accordance with an embodiment of the invention, and as will be further described below, an inner surface of the insert 300 is coated with a substance that receives and absorbs radiant EM energy from the radiant source 206 and converts the radiant EM energy to heat. The heat is transmitted via conduction through the wall of the insert 300 and, in one embodiment, directly transmitted via conduction to the analytical column 116, which is in direct contact with the outer surface of the insert 300. In an alternative embodiment, the analytical column 116 can be separated from the outer surface of the insert 300 by an air gap, in which case the heat from the insert 300 is transmitted to the analytical column 116 via convection. The insert 300 can be fabricated using, for example, aluminum, copper, or another material that can be treated, coated, or otherwise configured to absorb EM radiant energy on one surface, convert the radiant EM energy to heat, and transfer the heat to another surface.

Figure 3:
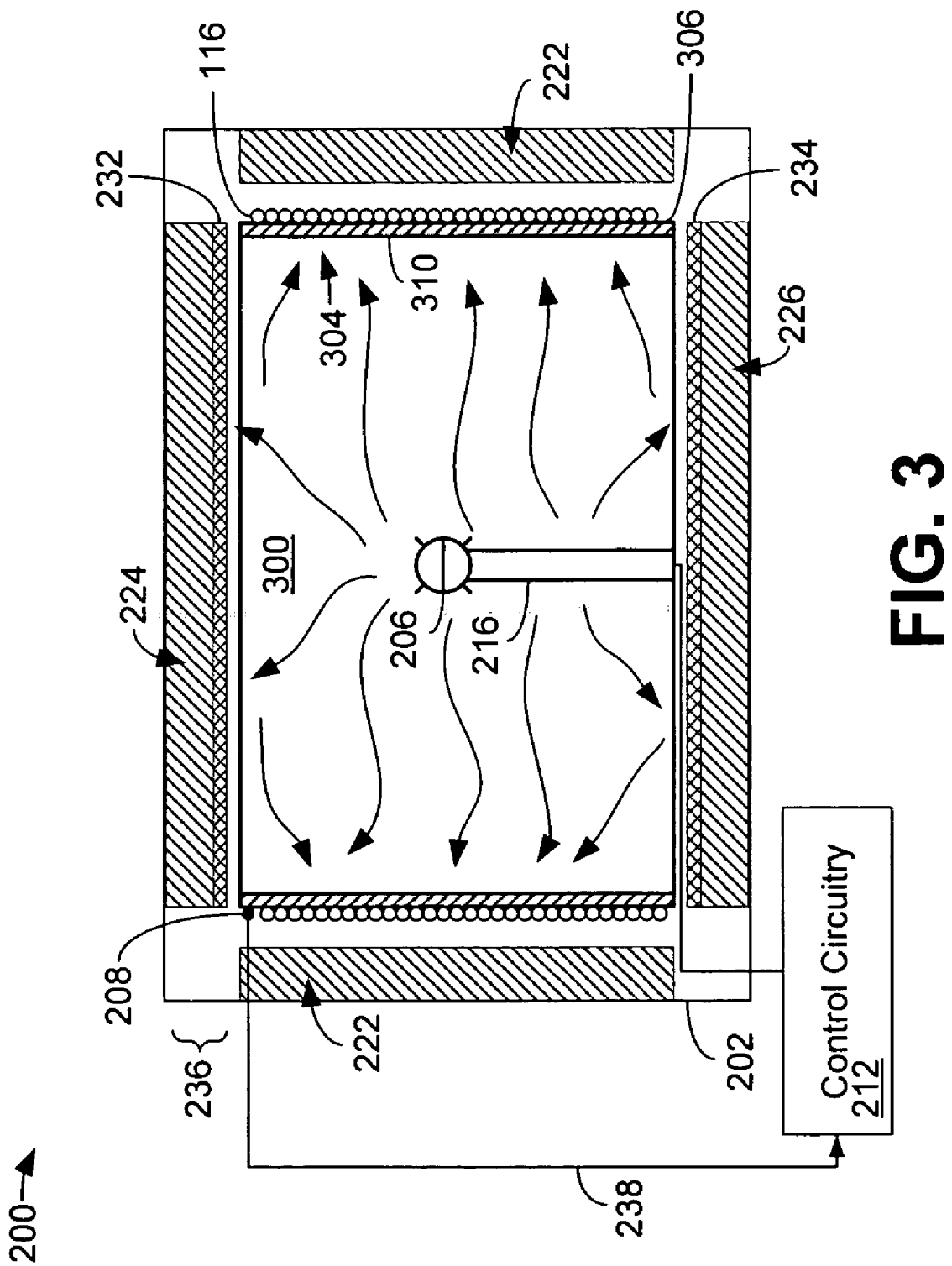
FIG. 3 is a schematic diagram illustrating a cross-sectional view of the radiant oven of FIG. 2.

FIG. 3 is a schematic diagram illustrating a cross-sectional view of the radiant oven 200 of FIG. 2. The radiant oven 200 includes a housing 202 in which the insert 300 is located. The housing 202 also includes the radiant source 206 and pedestal 216. In FIG. 3, the control circuitry 212 is depicted as a separate element, but in practice would likely be integrated within the housing 202.

As shown in FIG. 3, an analytical column 116 is tightly wrapped around an outer surface 306 of the insert 300. The temperature sensor 208 is secured, for example by bonding, to the outer surface 306 of the insert 300. An inner surface 304 of the insert 300 is treated or otherwise coated with a substance 310 that is configured to absorb the radiant EM energy emitted from the radiant source 206 and convert the radiant EM energy to heat. For example, the insert 300 can be aluminum and the inner surface 304 can be anodized to form a black, or dark, surface. The dark surface absorbs the radiant EM energy emitted from the radiant source 206 and converts the radiant EM energy to heat. The heat is transmitted through the wall of the insert 300 via conduction. The heat is then transferred to the analytical column 116 via, in this embodiment, conduction.

The radiant oven 200 also includes an upper reflector 232 and a lower reflector 234. The upper reflector 232 and the lower reflector 234 reflect radiant EM energy toward the inner surface 304 of the insert 300. The upper reflector 232 and the lower reflector 234 are preferably fabricated from a material that is reflective at the wavelength of the output of the radiant source 206. A typical IR reflector material is metal, preferably gold, which is highly resistant to oxidation. The radiant oven 300 also includes insulation portions 222, 224 and 226 to maintain the interior of the oven 200 at the desired temperature. In this embodiment, the insulation 224 and the upper reflector 232 form a cover 236.

The temperature sensor 208 precisely determines the temperature of the outer surface 306 of the insert 300, and therefore, the temperature of the analytical column 116. In another embodiment in which the analytical column 116 may be separated from the outer surface 306 of the insert 300 by an air gap, the temperature sensor 208 still provides a precise temperature measurement of the analytical column 116 by locating the temperature sensor in the air gap. A feedback signal provided from the temperature sensor 208 via connection 238 to the control circuitry 212 can be used to control the duty cycle at which the radiant source operates, and thereby precisely control the temperature in the radiant oven 200.

Positioning the insert 300 vertically in the oven 200 minimizes radiant energy gradients due to natural convection when the diameter of the insert is larger than the height. Positioning the insert so that the smaller of the diameter or the height in the direction of the plane of gravity minimizes the effects of natural convection. Alternatively, the radiant source 206 may be controlled, or modified, to minimize the effects of natural convection. In another embodiment, the insert may be positioned horizontally if the height is larger than the diameter.

Figure 4B:
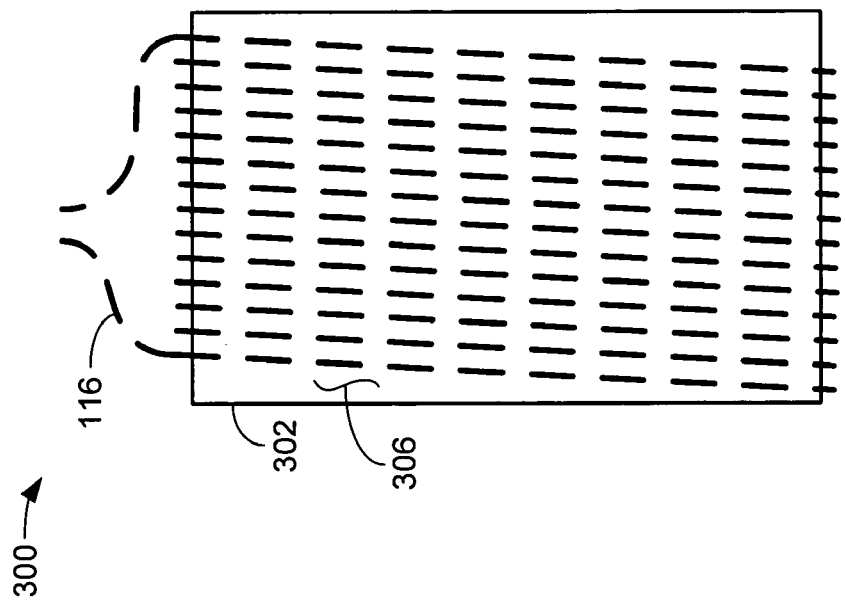
FIGS. 4A and 4B are schematic views collectively illustrating plan and side views of an embodiment of the insert of FIGS. 2 and 3.
Figure 4A:
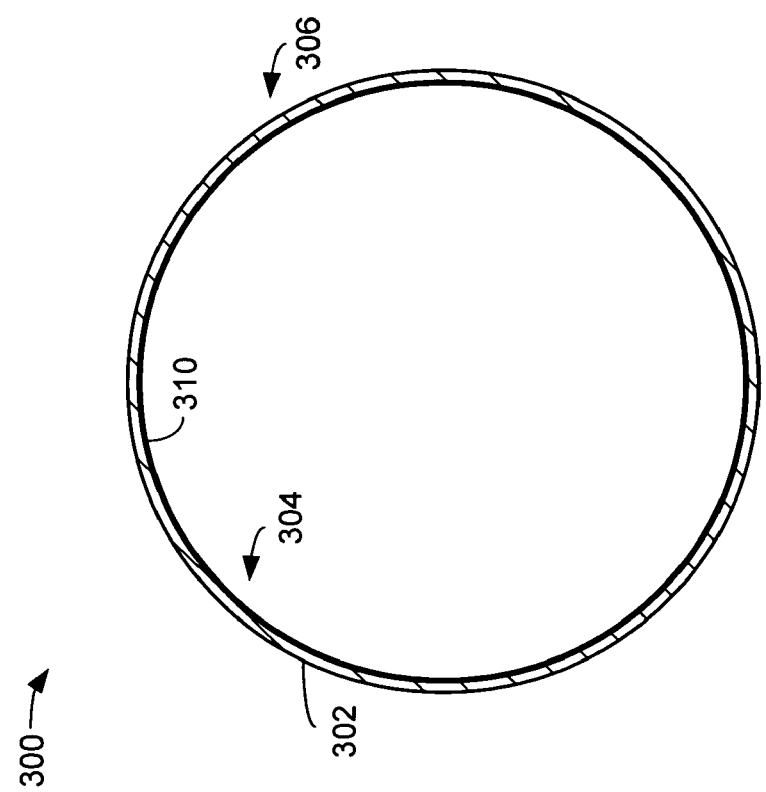

FIGS. 4A and 4B are schematic diagrams collectively illustrating plan and side views of an embodiment of the insert of FIGS. 2 and 3. FIG. 4A is a plan view of the insert 300. The insert 300 comprises a body 302 that can be fabricated from an efficient heat conductive material, such as, for example, aluminum or copper. The insert 300 comprises an inner surface 304 and an outer surface 306. In one embodiment, the insert 300 is aluminum and the inner surface 304 is anodized to form a dark, and preferably black, surface. The inner surface 304 is configured to absorb the radiant EM energy emitted by the radiant source 206 and convert the radiant EM energy to heat. The heat is conducted through the wall between the inner surface 304 and the outer surface 306. As described above, an analytical column 116 is either in direct contact with or in close proximity to the outer surface 306. In this manner, heat from the outer surface 306 is coupled, either via conduction or convection, to the analytical column 116. The dark inner surface 304 can alternatively have a coating 310 with a property that allows it to absorb the radiant EM energy emitted by the radiant source 206 and convert the radiant EM energy to heat.

FIG. 4B is a schematic side view of the insert 300 of FIG. 4A. An analytical column 116 is tightly wrapped around the outer surface 306 of the insert 300. In one embodiment, the insert 300 is approximately 123.5 millimeters (mm) in diameter, 66.9 mm in height and has a wall thickness of approximately 1 mm. However, the insert may take other shapes or profiles. For example, the insert 300 may take a shape in which the height is greater than the diameter.

Figure 5:
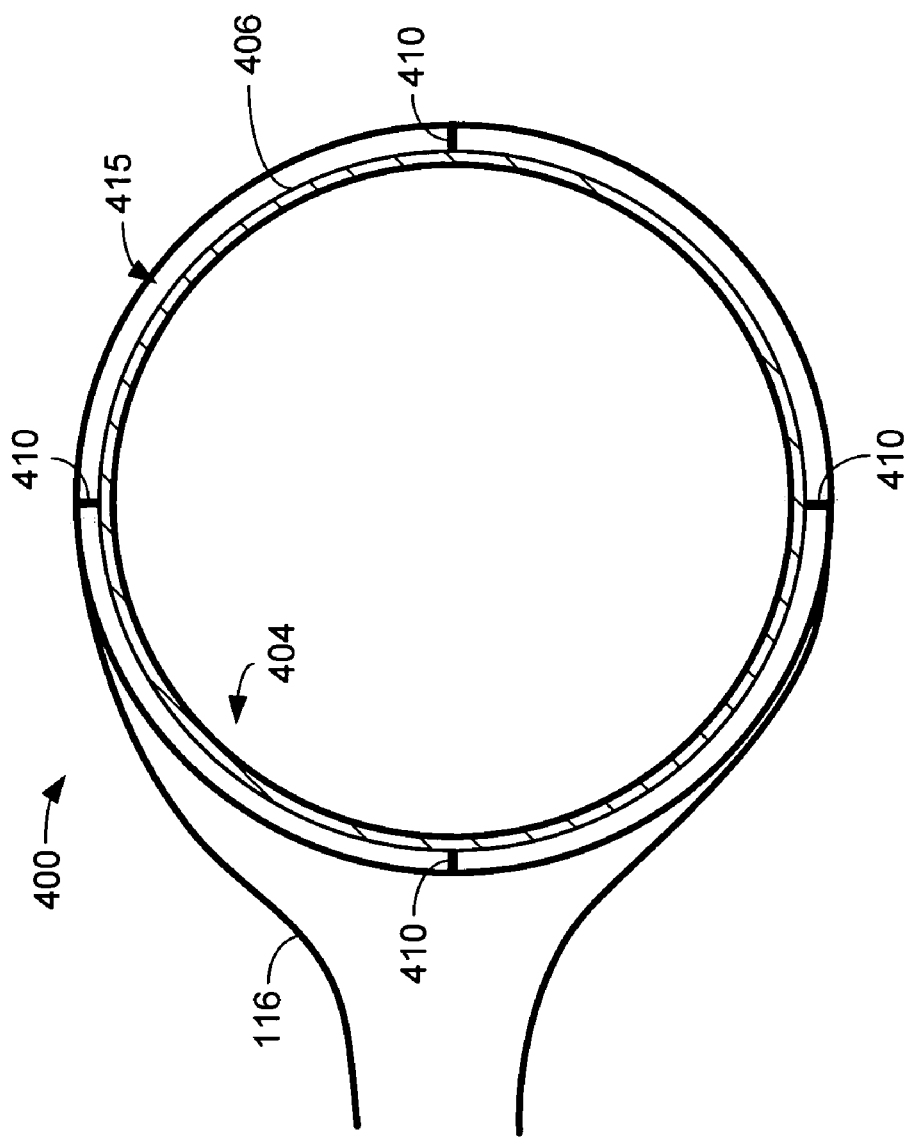
FIG. 5 is a schematic view illustrating an alternative embodiment of the insert of FIG. 3.

FIG. 5 is a schematic view illustrating an alternative embodiment 400 of the insert 300 of FIG. 3. In FIG. 5, the analytical column 116 is attached to the outer surface 406 of the insert 400 in such a way so that an air gap 415 is created between the analytical column 116 and the outer surface 406. For example, the analytical column 116 may be loosely wound around the outer surface 406 and attached using mounting points 410, approximately as shown. Heat is transferred from the outer surface 406 across the air gap 415 to the analytical column 116 via convection. While not in direct contact with the outer surface 406, the temperature of the analytical column 116 is still precisely controlled, and can be rapidly heated and cooled.

Figure 6:
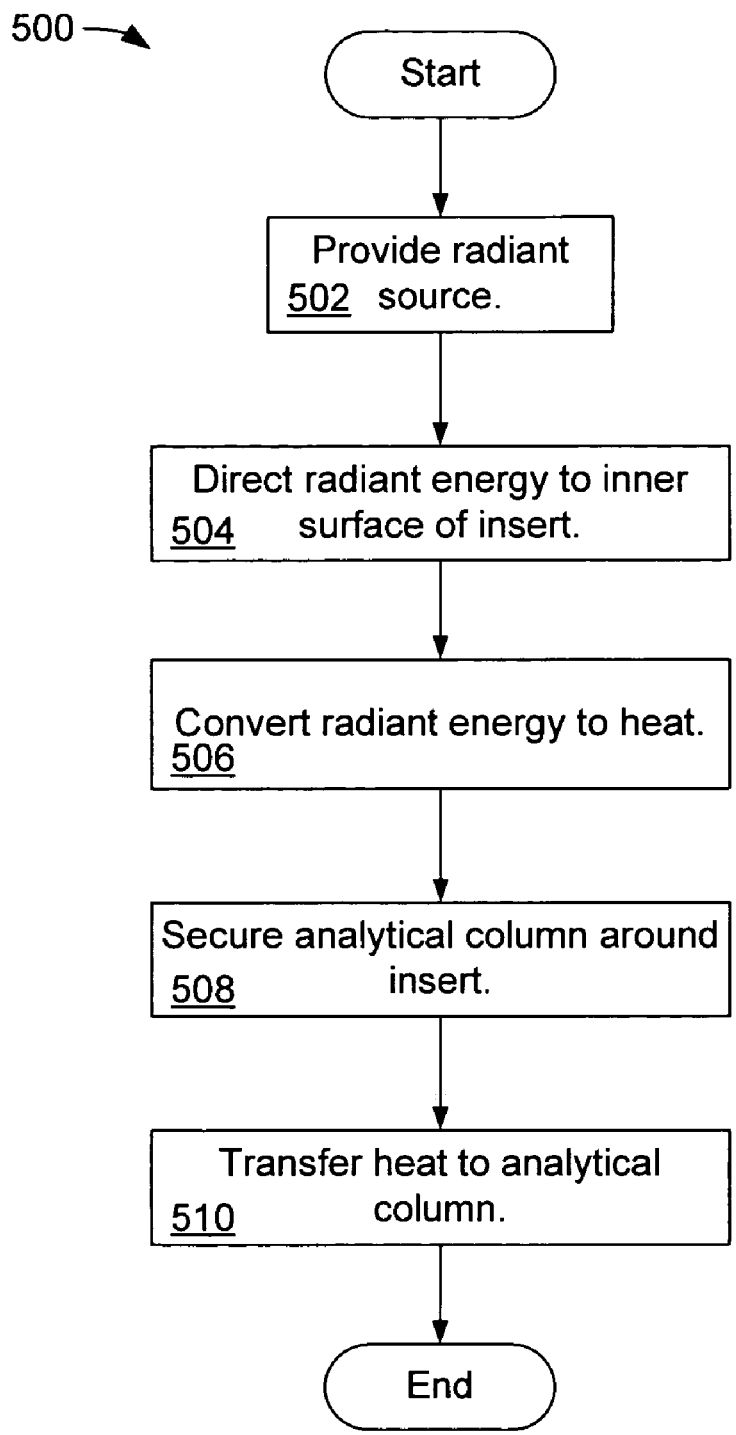
FIG. 6 is a flowchart illustrating the operation of a method for efficiently heating an analytical column.

FIG. 6 is a flowchart 500 illustrating the operation of a method for efficiently heating an analytical column. The blocks in the flowchart illustrate the operation of one embodiment of the invention and can be executed in the order shown, out of the order shown or in parallel. In block 502 a radiant source is provided. In block 504 the output of the radiant source is directed to the inner surface of the insert 300. In block, 506, the insert 300 converts the radiant energy to heat. In block 508, an analytical column is secured around the outer surface of the insert 300. In block 510, heat is transferred form the insert 300 to the analytical column 116.

The foregoing detailed description has been given for understanding exemplary implementations of the invention and no unnecessary limitations should be understood therefrom as modifications will be obvious to those skilled in the art without departing from the scope of the appended claims and their equivalents.

I claim:

1. A gas chromatograph, comprising:
   an inlet:
   an analytical column:
   a radiant oven that houses the column the radiant oven further comprising:
   a radiant energy source configured to provide one or more of ultraviolet, visible and infrared radiation;
   a cylindrical insert configured to at least partially enclose the radiant energy source and to receive the radiation and convert the radiation into heat; and
   wherein the analytical column receives the heat.

2. The gas chromatograph of claim 1, in which a first surface of the insert is configured to absorb the radiation.

3. The gas chromatograph of claim 1, in which the radiant energy source is a quartz halogen source.

4. The gas chromatograph of claim, in which the analytical column is in direct contact with the insert.

5. The gas chromatograph of claim 4, in which the insert couples the heat to the analytical column through conduction.

6. The gas chromatograph of claim 1, in which the analytical column is separated from the insert by an air gap.

7. The gas chromatograph of claim 6, in which the insert couples the heat to the analytical column through convection.

8. The gas chromatograph of claim 1, further comprising a temperature sensor in contact with the insert.

9. The gas chromatograph of claim 1, in which the insert has a diameter and a height and in which the smaller of the diameter and the height is oriented in the direction of gravity to minimize an effect of natural convection.

* * * * *

UNITED STATES PATENT AND TRADEMARK OFFICE
CERTIFICATE OF CORRECTION

PATENT NO. : 7,130,534 B1 Page 1 of 1
APPLICATION NO. : 11/111111
DATED : October 31, 2006
INVENTOR(S) : Miller, II It is certified that error appears in the above-identified patent and that said Letters Patent is hereby corrected as shown below:

In column 6, line 22, in Claim 1, after "inlet" delete ":" and insert -- ; --, therefor.

In column 6, line 23, in Claim 1, after "column" delete ":" and insert -- ; --, therefor.

In column 6, line 24, in Claim 1, after "column" insert -- , --.

In column 6, line 36, in Claim 4, delete "claim" and insert -- claim 1 --, therefor.

Signed and Sealed this

Twentieth Day of March, 2007

JON W. DUDAS
*Director of the United States Patent and Trademark Office*